US006850657B2

(12) United States Patent
Dhadwal et al.

(10) Patent No.: US 6,850,657 B2
(45) Date of Patent: Feb. 1, 2005

(54) CAPILLARY WAVEGUIDE FLUORESCENCE SENSOR

(75) Inventors: Harbans S. Dhadwal, Setauket, NY (US); Josephine Y. Aller, Stony Brook, NY (US); Paul F. Kemp, Lindenhurst, NY (US)

(73) Assignee: The Research Foundation of State University of New York, Albany, NY (US)

( * ) Notice: Subject to any disclaimer, the term of this patent is extended or adjusted under 35 U.S.C. 154(b) by 65 days.

(21) Appl. No.: 10/360,114

(22) Filed: Feb. 7, 2003

(65) Prior Publication Data

US 2003/0152308 A1 Aug. 14, 2003

Related U.S. Application Data (60) Provisional application No. 60/355,143, filed on Feb. 8, 2002.

(51) Int. Cl.[7] .................................................. G02B 6/00
(52) U.S. Cl. ........................ 385/12; 385/13; 385/147; 356/246
(58) Field of Search .......................... 3685/12, 13, 125, 3685/147; 356/246, 318; 436/172

(56) References Cited

U.S. PATENT DOCUMENTS

| 4,447,546 A | 5/1984 | Hirschfeld .................. 436/527 |
| 4,716,121 A | 12/1987 | Block et al. ................ 436/514 |
| 5,416,879 A | 5/1995 | Liu ............................ 385/125 |
| 6,137,117 A | 10/2000 | Feldstein et al. ........... 250/573 |
| 6,252,657 B1 | 6/2001 | Bohnenkamp ............... 356/244 |
| 6,323,042 B1 | 11/2001 | Narang et al. .............. 436/514 |
| 6,332,049 B1 * | 12/2001 | Dasgupta ..................... 385/12 |
| 6,526,188 B2 * | 2/2003 | Dourdeville et al. .......... 385/12 |

* cited by examiner

*Primary Examiner*—Phan T. H. Palmer
(74) *Attorney, Agent, or Firm*—Hoffmann & Baron, LLP (57) ABSTRACT

A capillary waveguide fluorescence sensor which includes a capillary and an optical/fluid connector connected to an end of the capillary. The optical/fluid connector includes a fluid sample injection port for longitudinally injecting a fluid sample into the capillary bore and at least one optical fiber for either longitudinally delivering light energy into the capillary or longitudinally collecting fluorescence emission from the fluid sample injected into the capillary bore. The sensor may also include at least one capillary outer surface collection optical fiber for perpendicularly collecting fluorescence emission from the fluid sample injected into the capillary bore. The capillary outer surface collection optical fiber is positioned adjacent the outer surface of the capillary wall such that the central axis of the collection optical fiber is substantially perpendicular to the central axis of the capillary bore. In a method for sensing fluorescence emission from a fluid sample, the fluid sample is longitudinally injected into a bore of a capillary and the fluid sample is excited by longitudinally delivering light energy into the capillary. Fluorescence emission caused by the excitation from the fluid sample may be collected by at least one optical fiber positioned substantially perpendicularly to the central axis of the capillary bore or it may be longitudinally collected by at least one optical fiber positioned substantially parallel with the central axis of the capillary bore.

33 Claims, 6 Drawing Sheets

CAPILLARY WAVEGUIDE FLUORESCENCE SENSOR

CROSS-REFERENCE TO RELATED APPLICATION

This application claims the benefit of U.S. Provisional Application No. 60/355,143, filed on Feb. 8, 2002.

This invention was made with government support under Grant No. OCE-0083 193 awarded by the National Science Foundation (NSF). The government may have certain rights in the invention.

BACKGROUND OF THE INVENTION

The present invention relates generally to biosensors, and more particularly, to a fluorescence sensor that utilizes a capillary waveguide.

Fluorescence sensors having a capillary as a light guiding device are effective analytical tools used to measure the concentrations of different analytes as well as for detecting the presence of nucleic acids such as DNA. Particularly useful applications include DNA sequencing, genetic analysis, medical diagnosis and forensics. The basic approach is to monitor a fluid sample containing the target analyte or nucleic acids by illuminating a region of a capillary core with a laser and measuring the induced fluorescence as molecules move through the illuminated region.

One type of fluorescence sensor utilizes a direct detection process, wherein the target fluid sample is provided with a fluorescent marker prior to injection of the sample into the capillary. Another type of fluorescence sensor utilizes an indirect detection process, wherein a surface of the capillary that will come in contact with the target sample is coated with a layer of probe molecules.

Nucleic acid based sensors offer a high degree of selectivity and stability. Detection is based on specific hybridization between a single-stranded nucleic acid oligonucleotide "probe" sequence and the sample "target" sequence to be detected. The probe is typically immobilized on a substrate, such as an optical fiber or a planar waveguide. In fluorescence based sensors, target sequences are tagged with fluorescent molecules. In situ hybridization, standard Watson-Crick base pairing for strand annealing, allows detection of the targeted species. Denaturing, through elevated temperatures or through the use of denaturants, allows the sensor to be used for repeated detection.

Figure 1:
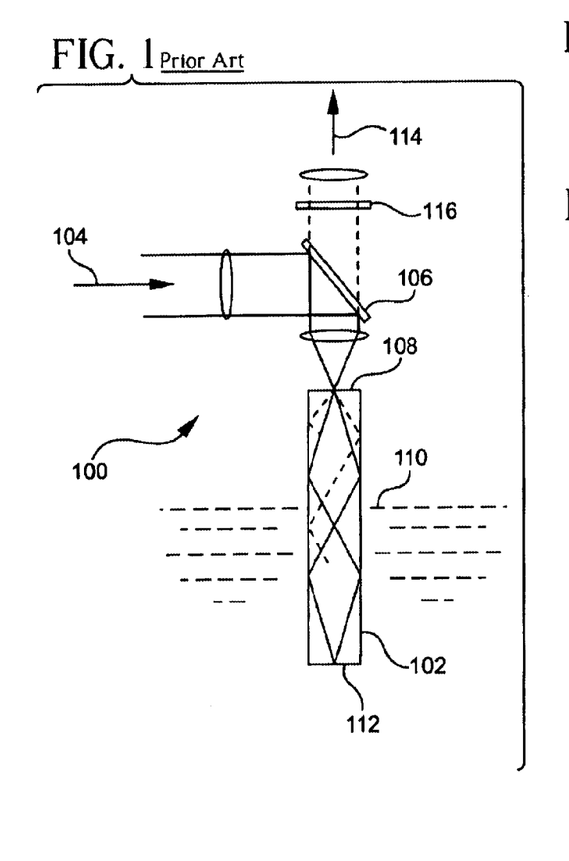
FIG. 1 is a schematic drawing of a conventional prior art fluorescence sensor.

A conventional fluorescence sensor 100, as depicted in FIG. 1, employs a coaxial optical geometry for excitation and collection. Such first generation sensors used an unclad quartz rod 102 typically 0.5 to 1 mm in diameter and several centimeters in length. The outer surface of the rod 102 is coated with a probe sequence. A light energy source (not shown) is positioned perpendicularly to the quartz rod 102 and directs excitation light 104 to a dichroic beam splitter 106, which redirects the light longitudinally into a proximal end 108 of the rod, which is immersed in a fluid sample 110 containing the target sequence. The fluorescence emission 114 is collected from the proximal end 108 after passing through a band pass optical filter 116.

The fluorescence captured by the guided modes of the optical rod arrangement shown in FIG. 1 is critically dependent on the numerical aperture (NA) of the excitation and collection optics. Matching of the optical system NA to the sensor NA, which is determined by the index of the refraction of the core and the sample, is critical to successful functioning of the sensor. Traditionally, for ease of use, a backward scheme is preferred such that the fluorescence is collected from the proximal end surface of the fiber contrary to the preferred collection from the distal end surface.

Fiber optic sensors have gone through an evolution over the last two decades. Most designs have sought to seek improvement in sensor sensitivity through the use of tapered distal fiber ends, while others have introduced a tapered region in the center of a longer length of fiber. The tapered designs have faced the problem of mismatch between the V-number of the optical fiber in the sensor and guiding regions. To overcome some of these difficulties single mode fibers with etched claddings, exposing a longitudinal section have been proposed. Other sensors have utilized planar waveguides, fiber array imaging, and optical microcavities for containing optical wave fields.

In the last decade silica micro-capillaries have been fast replacing optical fibers in the development of analytical sensors for use in various applications. The capillary provides a unique combination of supporting both fluid flow and optical light propagation. In particular, micro-capillaries have found extensive use in DNA sequencing using gel electrophoresis. For biosensor applications, the probe sequence(s) can be covalently bonded to the interior surface of the capillary to provide detection of target sequence(s) flowing through the capillary. Coating on the interior surface also protects against accidental damage during handling.

In general, the sensitivity of fluorescence based sensors may be specified in two ways: first, by the lowest concentration of detectable target; and second, by tracking of small changes in the target concentration. In the first case, the limit is determined by system electronics, while in the second case, the limit is dependent on the stability of the various system components, such as the power stability of the excitation source. In practice, however, the limit of detection is determined by the amount of stray light bleeding into the emission band of the target species. Optimal design based on a combination of optical filtering, high speed optics and separation of excitation and collection paths is necessary to achieve limits approaching concentrations below ng/ml.

Figure 2A:
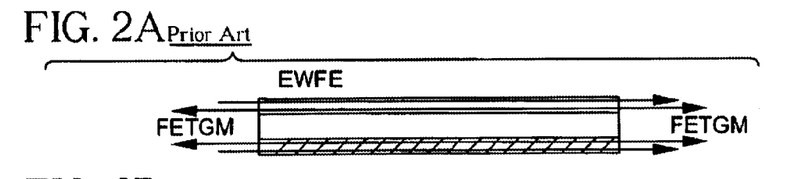
FIGS. 2a–2d are schematic diagrams of prior art optical configurations used in capillary based fluorescence sensors.

FIGS. 2a–2d illustrate some of the other prior art optical configurations which are used in capillary based fluorescence sensors. Traditionally, a coaxial arrangement, as shown in FIG. 2a, is utilized where the surface molecules are illuminated by evanescent wave field excitation (EWFE) and a portion of fluorescence which tunnels into the guided modes (FETGM) of the capillary wall is captured at either (or both) ends of the capillary. This configuration, while providing uniform illumination of the hybridized molecules along the entire capillary length has the highest excitation background and requires considerable optical filtering. Additionally, this arrangement does not allow independent optimization of excitation and emission geometries.

Figure 2B:
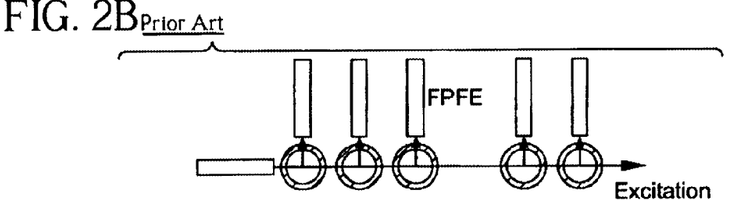

FIG. 2b illustrates the arrangement used for capillary gel electrophoresis. In this arrangement, 90-degree separation between the excitation and fluorescence emission paths (FPFE) is essential to achieving sensitivities approaching $10^{-12}$ M.

Figure 2C:
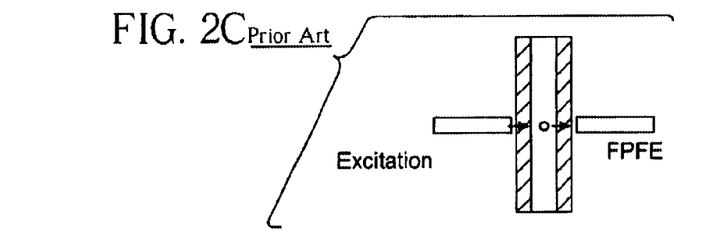

FIG. 2c shows a forward transmitting geometry which has been used for detecting $CO_2$ changes through either fluorescence or absorption. This arrangement typically uses grating couplers, printed on the outer surface of the capillary, for exciting higher order modes in the capillary wall and for interrogating the guided fluorescence emission. Prism couplers are also typically employed for selectively coupling energy into and out from the planar waveguides.

Figure 2D:
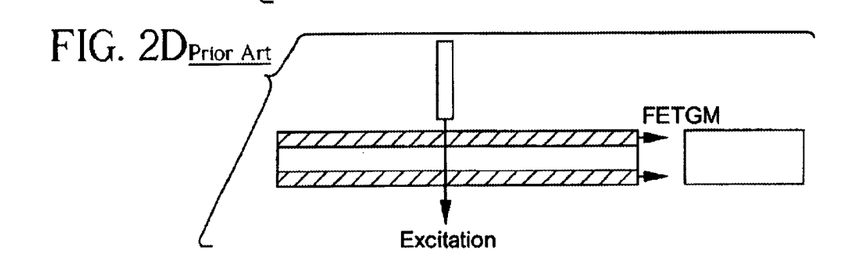

FIG. 2d illustrates an orthogonal arrangement. Excitation energy is launched into the waveguide at right angles to the capillary surface and the integrated fluorescence energy tunneled into the guided modes of the capillary wall is collected at the capillary end face. This arrangement does not provide uniform and efficient illumination of the hybridized target molecules along the entire capillary length.

It would be desirable to provide a simple biosensor without the aforementioned drawbacks. In particular, it would be desirable to provide an accurate capillary waveguide fluorescence device that is relatively compact, simple in construction and requires a smaller volume of target sample.

SUMMARY OF THE INVENTION

The present invention is a capillary waveguide fluorescence sensor which includes a capillary and an optical/fluid connector connected to one end of the capillary. The capillary has a capillary wall including an inner surface defining a capillary bore and an outer surface. The optical/fluid connector includes a fluid sample injection port for longitudinally injecting a fluid sample into the capillary bore and at least one optical fiber for either longitudinally delivering light energy into the capillary or longitudinally collecting fluorescence emission from the fluid sample injected into the capillary bore. Preferably, the optical/fluid connector includes a delivery optical fiber for longitudinally delivering light energy into the capillary and a collection optical fiber for longitudinally collecting fluorescence emission from the fluid sample injected into the capillary bore. The inner surface of the capillary wall may be coated with a layer of probe molecules.

In a preferred embodiment, the sensor further includes at least one capillary outer surface collection optical fiber for collecting fluorescence emission from the fluid sample injected into the capillary bore. The capillary outer surface collection optical fiber is positioned adjacent the outer surface of the capillary wall such that the central axis of the collection optical fiber is substantially perpendicular to the central axis of the capillary bore. Preferably, the sensor includes a linear array of capillary outer surface collection optical fibers for collecting fluorescence emission from the fluid sample injected into the capillary bore. The linear array of capillary outer surface collection optical fibers includes a plurality of aligned collection optical fibers positioned adjacent the outer surface of the capillary wall such that the central axes of the collection optical fibers are substantially perpendicular to the central axis of the capillary bore.

The optical fiber in the optical/fluid connector may be positioned to longitudinally deliver the light energy directly into or longitudinally collect the fluorescence emission directly from the capillary bore at the end of the capillary. It may also be positioned in the optical/fluid connector to longitudinally deliver the light energy directly into or longitudinally collect the fluorescence emission directly from the capillary wall between the inner and outer surfaces at the end of the capillary.

In an alternative embodiment, the fluorescence sensor includes a capillary, a fluid connector connected to an end of the capillary and at least one capillary outer surface collection optical fiber for collecting fluorescence emission from a fluid sample injected into the capillary bore. The capillary has a capillary wall including an inner surface defining a capillary bore and an outer surface. The fluid connector includes a fluid sample injection port for longitudinally injecting a fluid sample into the capillary bore and the capillary outer surface collection optical fiber is positioned adjacent the outer surface of the capillary wall such that the central axis of the collection optical fiber is substantially perpendicular to the central axis of the capillary bore.

In a preferred alternative embodiment, the fluid connector further includes at least one optical fiber for either longitudinally delivering light energy into the capillary or longitudinally collecting fluorescence emission from the fluid sample injected into the capillary bore. The fluid connector preferably includes both a delivery optical fiber for longitudinally delivering light energy into the capillary and a collection optical fiber for longitudinally collecting fluorescence emission from the fluid sample injected into the capillary bore. Preferably, the fluorescence sensor has a linear array of capillary outer surface collection optical fibers for collecting fluorescence emission from the fluid sample injected into the capillary bore. The linear array of capillary outer surface collection optical fibers includes a plurality of aligned collection optical fibers positioned adjacent the outer surface of the capillary wall such that the central axes of the collection optical fibers are substantially perpendicular to the central axis of the capillary bore.

The present invention also involves a method for sensing fluorescence emission from a fluid sample. The method includes the steps of longitudinally injecting the fluid sample into a bore of a capillary having an inner surface and an outer surface, exciting the fluid sample by longitudinally delivering light energy into the capillary and collecting fluorescence emission caused by the excitation from the fluid sample with at least one optical fiber positioned substantially perpendicularly to the central axis of the capillary bore. Again, the light energy may be longitudinally delivered directly into the capillary bore at an end of the capillary, or it may be longitudinally delivered into a wall of the capillary between the inner and outer surfaces. A preferred method further includes the step of collecting fluorescence emission caused by the excitation from the fluid sample with at least one optical fiber positioned substantially parallel to the central axis of the capillary bore.

An alternative method for sensing fluorescence emission from a fluid sample includes the steps of longitudinally injecting the fluid sample into a bore of a capillary having an inner surface and an outer surface, exciting the fluid sample by longitudinally delivering light energy into the capillary and longitudinally collecting fluorescence emission caused by the excitation from the fluid sample with at least one optical fiber positioned substantially parallel with the central axis of the capillary bore. A preferred alternative method further includes the step of perpendicularly collecting fluorescence emission caused by the excitation from the fluid sample with at least one optical fiber positioned substantially perpendicularly to the central axis of the capillary bore.

As a result of the present invention, a compact capillary waveguide fluorescence sensor is provided. The sensor of the present invention allows for integration of optical excitation and fluid flow within the same capillary, thereby reducing the volume of target sample. Also, integrating fluid flow and optical fibers into a miniature fiber optic connector reduces complexity and improves system reliability. Additionally, fluorescence emission may be collected by means of a plurality of optical fibers positioned orthogonal to the capillary axis. Moreover, a plurality of optical fibers in the miniature fiber optic connector permits: i) axial transmission of the excitation energy; ii) axial collection of fluorescence emission; and iii) axial injection of the target sample into the capillary.

A preferred form of the capillary waveguide fluorescence sensor of the present invention, as well as other embodiments, objects, features and advantages of this invention will be apparent from the following detailed description of illustrative embodiments thereof, which is to be read in connection with the accompanying drawings. It is to be understood, however, that the drawings are designed as an illustration only and not as a definition of the limits of the invention.

DETAILED DESCRIPTION OF THE PREFERRED EMBODIMENTS

Figure 3:
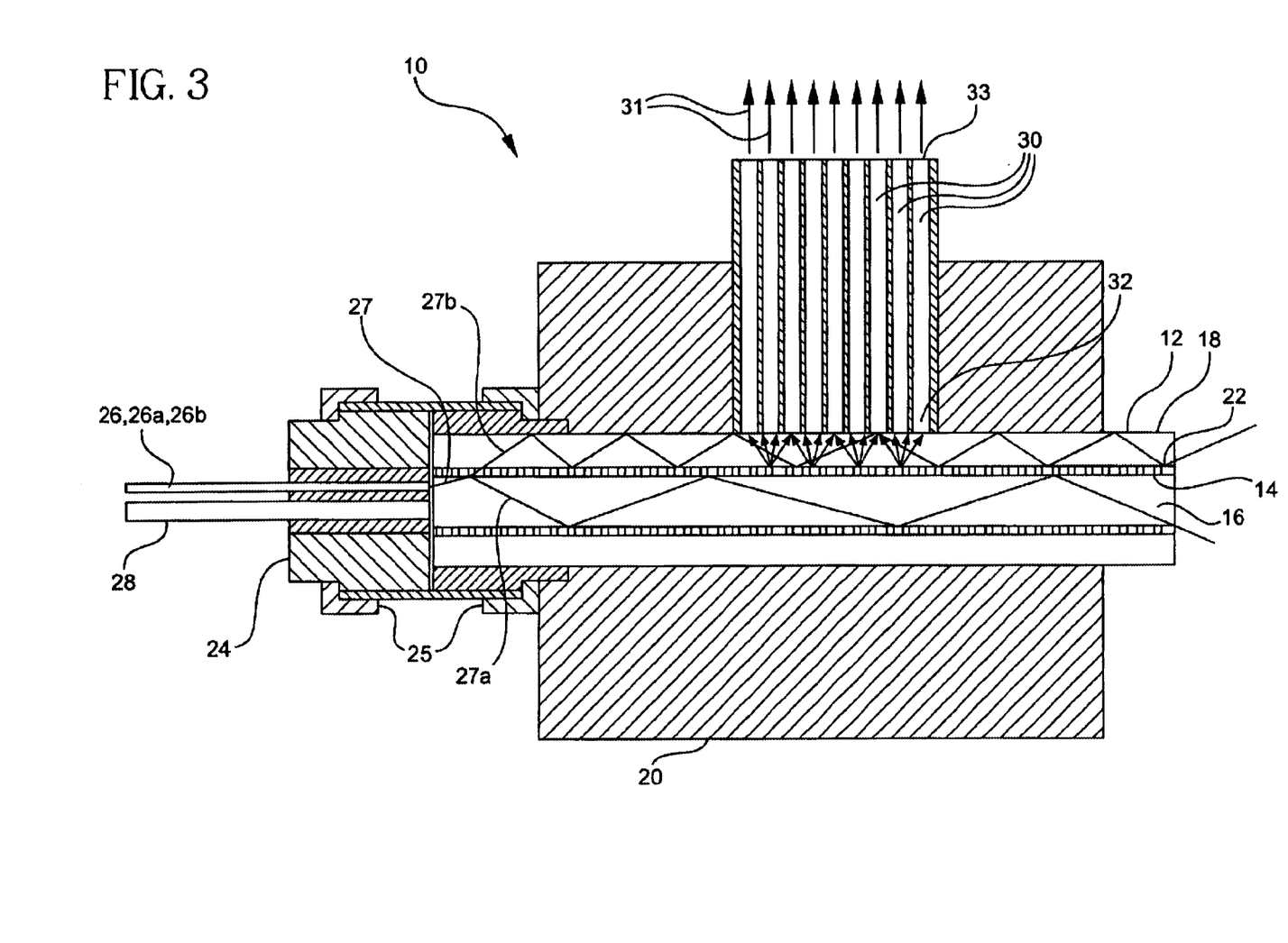
FIG. 3 is a cross-sectional view of a preferred embodiment of the capillary waveguide fluorescence sensor formed in accordance with the present invention.

Referring first to FIG. 3, a capillary waveguide fluorescence sensor 10 formed in accordance with the present invention is shown. The sensor 10 generally includes a microbore thin wall capillary 12 having an inner surface 14 defining a bore 16 and an outer surface 18. The capillary 12 is preferably a silica thin wall capillary having an inner diameter of about 1.0 mm and an outer diameter of about 1.3 mm. The capillary is preferably contained in a solid cylindrical housing 20 to prevent stray light from entering the capillary.

The sensor 10 can be configured for either direct detection of fluorescence from target species contained in a sample fluid flowing through the microbore capillary 12 or it can be configured for indirect detection by using suitable coatings on the interior surface 14 of the capillary. For indirect detection, the interior surface 14 defining the bore 16 of the capillary 12 is coated with a layer of probe molecules 22. The coating can be applied in any conventional manner.

Thus, a typical capillary 12 for use in the present invention may include a series of cylindrical shells with different refractive indices. The bore 16 provides a channel for transport of the target sequence in a fluid stream. Next, if configured for indirect detection, is the thin layer of coating 22, typically, of the order of 100 nm, containing an immobilized probe sequence. This layer 22 preferably consists of biotin covalently bonded to the silica inner surface 14 of the capillary 12 and a freely attached probe sequence, the length of which is defined in terms of the number of base-pairs used for recognizing the target sequence. The effective thickness of the coating layer 22 is determined by the total length of the sequence. For example, a probe length of 15 bases corresponds to a thickness on the order of 45 nm. The upper bound is determined by the penetration depth of the evanescent wave, which is smaller than one wavelength, i.e. typically 532 nm. The capillary wall is preferably made from pure silica and has a refractive index close to 1.5. The outer surface 18 of the capillary can be further coated or immersed in another fluid.

Connected to at least one end of the capillary 12 is an optical/fluid connector 24 which provides a means for introducing both the optical excitation and the fluid containing the target species through the capillary and a means for longitudinally collecting the fluorescence emission. A second optical/fluid connector 24 can be connected to the opposite end of the capillary 12 to provide for delivery of light energy, collection of fluorescence and/or injection of fluid samples from either or both ends of the capillary. The optical/fluid connector 24 may be attached to the capillary 12 by threaded couplings 25.

The optical/fluid connector 24 includes at least one fluid injection port 28 positioned within the diameter of the capillary bore 16 for injecting the fluid sample into the capillary bore 16. The optical/fluid connector 24 further includes at least one optical fiber 26 for either delivering excitation light energy 27, such as laser light, to the capillary 12, or collecting fluorescence emission from the fluid sample injected into the capillary bore. The optical fiber 26 and the fluid injection port 28 are secured in the optical/fluid connector 24 such that their axes are generally parallel to the central axis of the capillary bore 16. In this manner, light delivered to the capillary 12 by a delivery optical fiber 26a is delivered longitudinally with respect to the central axis of the capillary bore 16 and in the same direction as the fluid sample injected from the fluid injection port 28. Similarly, if the fiber is a collection optical fiber 26b, fluorescence emission is collected longitudinally with respect to the central axis of the capillary bore 16 and in the same direction as the fluid sample injected from the fluid injection port 28.

A light excitation source (not shown) can be an inexpensive 3 mW solid-state laser diode operating at a wavelength of 532 nm. Excitation of the bound fluorescent molecules can be achieved either by total or partial reflection at the interior surface 14 of the capillary 12. The latter allows for Fresnel loss (or additional absorption) at the coating/fluid interface. The capillary 12 is a weakly guiding optical structure, which over short lengths behaves as an optical fiber. Essentially, the number of reflections is proportional to the NA of the source and inversely proportional to the inner diameter of the capillaries. Additionally, the inner region is weakly guiding and more than 99.5% of the incident power is lost at each reflection, thereby negating any advantage from integrating over a finite capillary length.

Alternatively, optical energy can be launched directly into the capillary wall, which is strongly guiding. Through this method very uniform evanescent wave excitation along the length of the capillary can be achieved. The excitation of the coating layer is predominantly provided by the evanescent wave resulting from the various optical modes propagating in the capillary wall.

Figure 4:
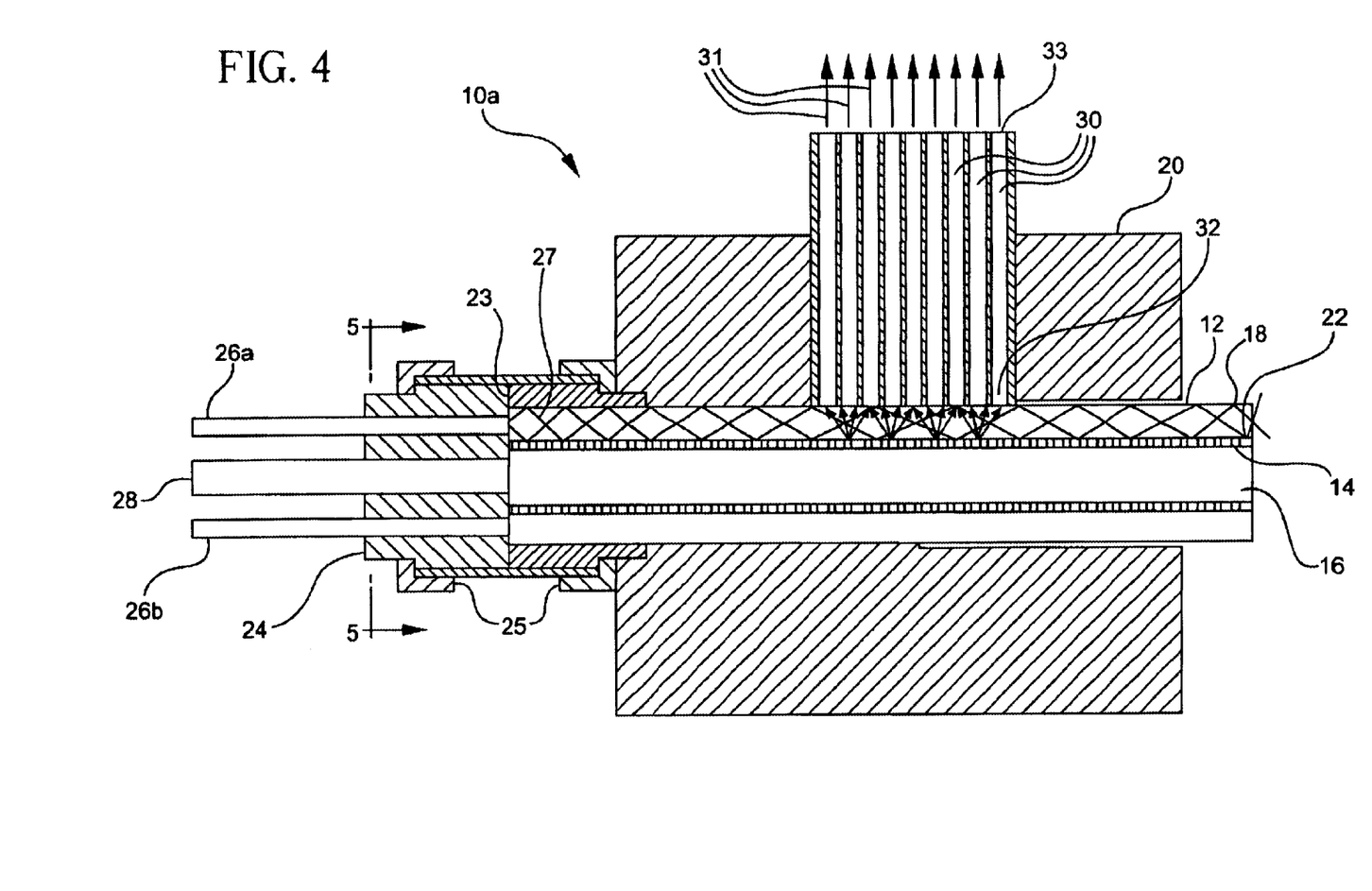
FIG. 4 is a cross-sectional view of an alternative embodiment of the capillary waveguide fluorescence sensor formed in accordance with the present invention.

Thus, a delivery optical fiber 26 may be positioned in the optical/fluid connector 24 within the diameter of the capillary bore 16 to longitudinally deliver light 27 directly into the bore, as shown in FIG. 3, or a delivery optical fiber 26a may be positioned outside the diameter of the bore to longitudinally deliver light into the capillary wall between the inner surface 14 and the outer surface 18 of the capillary, as shown in FIG. 4. When the light 27 is longitudinally delivered directly in the capillary bore 16, as shown in FIG. 3, the capillary 12 acts as a wave guide wherein a portion of the light 27a travels within the bore, while a portion of the light 27b enters and travels in the capillary wall between the inner surface 14 and the outer surface 18. When the light is delivered into the capillary wall of the sensor 10a, as shown in FIG. 4, the capillary 12 guides the light wave 27 between the inner and outer surfaces 14 and 18 along the length of the capillary.

Figure 5:
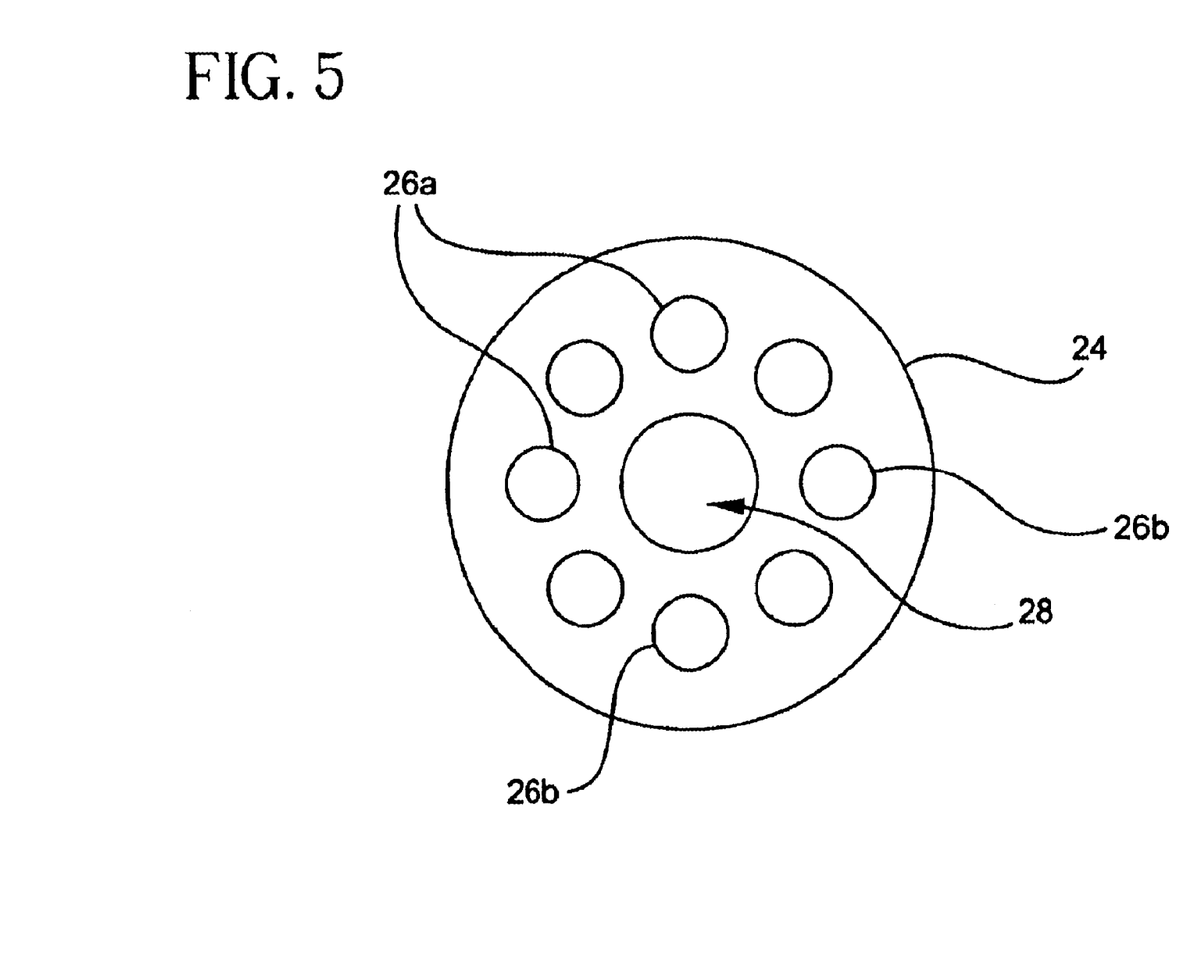
FIG. 5 is a cross-sectional view of the optical fluid connector shown in FIG. 4 taken along the line 5—5.

In both embodiments, it is preferred to have an arrangement of a plurality of optical fibers 26a and 26b positioned around the central axis of the capillary bore 16, as shown in the cross-sectional view of FIG. 5. Preferably, some of the fibers are excitation light delivery optical fibers 26a and the others are fluorescence emission collecting optical fibers 26b.

The diameter and NA of the delivery or launching fiber 26a can be matched to the capillary wall thickness and NA. A ring of such fibers 26a and 26b can fill the entire distal end face 23 of the capillary 12. For typical values of refractive indices of the aqueous fluid sample and silica, the NA of the capillary wall sensor (CWS) 10a is preferably about 0.67. High NA optical fibers typically have values approaching 0.48 but the diameters tend to be on the order of 300 microns. Other schemes such as tapering and angle polishing may be used to increase the NA of the optical fiber. In a preferred embodiment, optical fibers with NA=0.39 and core/cladding diameter of 110/1125 microns are used.

The multi-purpose optical/fluid connector 24 of the present invention provides injection of fluid into the capillary 12, evanescent wave excitation of the immobilized molecules, and, if needed, collection of the evanescently coupled emission into the guided modes of the capillary wall. In the first embodiment shown in FIG. 3, the connector 24 contains a single optical fiber 26 for transmitting the excitation energy into the interior of the capillary bore 16 and a stainless steel tube injection port 28 for fluid flow. In the first embodiment, excitation of the coating layer 22 is achieved through partial reflections. In the second embodiment shown in FIGS. 4 and 5, a stainless steel tube injection port 28 is located at the center of the connector 24 allowing fluid to be introduced into the capillary bore 16. A ring of optical fibers 26a and 26b is positioned in the connector 24 such that the optical surfaces of the fibers match up with the capillary wall between the inner surface 14 and the outer surface 18. In this way, the optical fibers 26a and 26b are not exposed to the fluid at any time. Some of the optical fibers 26a can be used for illuminating the capillary wall either at the same wavelength or at different excitation wavelengths. Similarly, the remaining fibers 26b can be used for collecting the fluorescence emission trapped in the bounded modes of the capillary wall.

In either embodiment, 22AWG stainless steel tubing can be used for the injection port 28 for fluid flow. In the embodiment shown in FIG. 3, a single fiber with a diameter of 300 $\mu$m and NA=0.39(Spectran Speciality Optics) can be used. In the embodiment shown in FIG. 4 with a plurality of optical fibers surrounding the stainless steel tubing, 110/1125 $\mu$m fibers with a NA=0.29(Spectran Speciality Optics HCP110T) can be used.

Fluorescence from immobilized molecules in the coating layer propagates freely through the capillary wall and emanates from the outer surface of the capillary. Some of the fluorescence, particularly emission at higher angles, is coupled into the guided modes of the capillary wall via quantum tunneling. Preferably, the present invention utilizes optical configurations which allow collection of both types of fluorescence signals for maximizing free fluorescence.

Free propagating fluorescence emission emanating from the surface of the capillary can be collected by a single or, more preferably, by a plurality of high NA optical fibers positioned above the capillary surface and optically coupled to an imaging detector. Optimal design of the CWS is concerned with defining the dimensions of the capillary that provides the maximum transmission of the free propagating fluorescence from the immobilized molecules in the coating layer/fluid interface.

Thus, the sensor 10, 10a further preferably includes at least one capillary outer surface collection optical fiber 30 secured in the cylindrical housing 20 so that its light receiving end 32 is adjacent the outer surface 18 of the capillary. Preferably, the sensor 10, 10a includes a linear array of a plurality of collection optical fibers 30 for collecting the fluorescence emission 31 from the fluid sample, as shown in FIGS. 3 and 4. The capillary outer surface collection optical fibers 30 are preferably aligned in a plane substantially perpendicular (orthogonal) to the capillary axis for perpendicularly collecting the axial fluorescence emission. The collection optical fibers 30 are in turn connected at an opposite end 33 to a conventional compact photodetector system (not shown in FIGS. 3 and 4), which includes emission filters, a photomultiplier and data processing equipment for measuring and analyzing the collected fluorescent data.

Since a typical micro-capillary which can be used in the sensor 10, 10a of the present invention has inner and outer diameters of a few hundred microns, the use of geometrical optics to analyze the optical properties is acceptable. A capillary with a wall thickness of 150 $\mu$m and a refractive index of 1.5 has a V-parameter of 195. In a planar geometry this structure would support over twenty thousand electromagnetic modes. In order to obtain an optimal design, ray tracing software that allows fluorescent point sources to be located at the coating/fluid interface in the interior region of the capillary waveguide is preferred.

EXAMPLE

Figure 6:
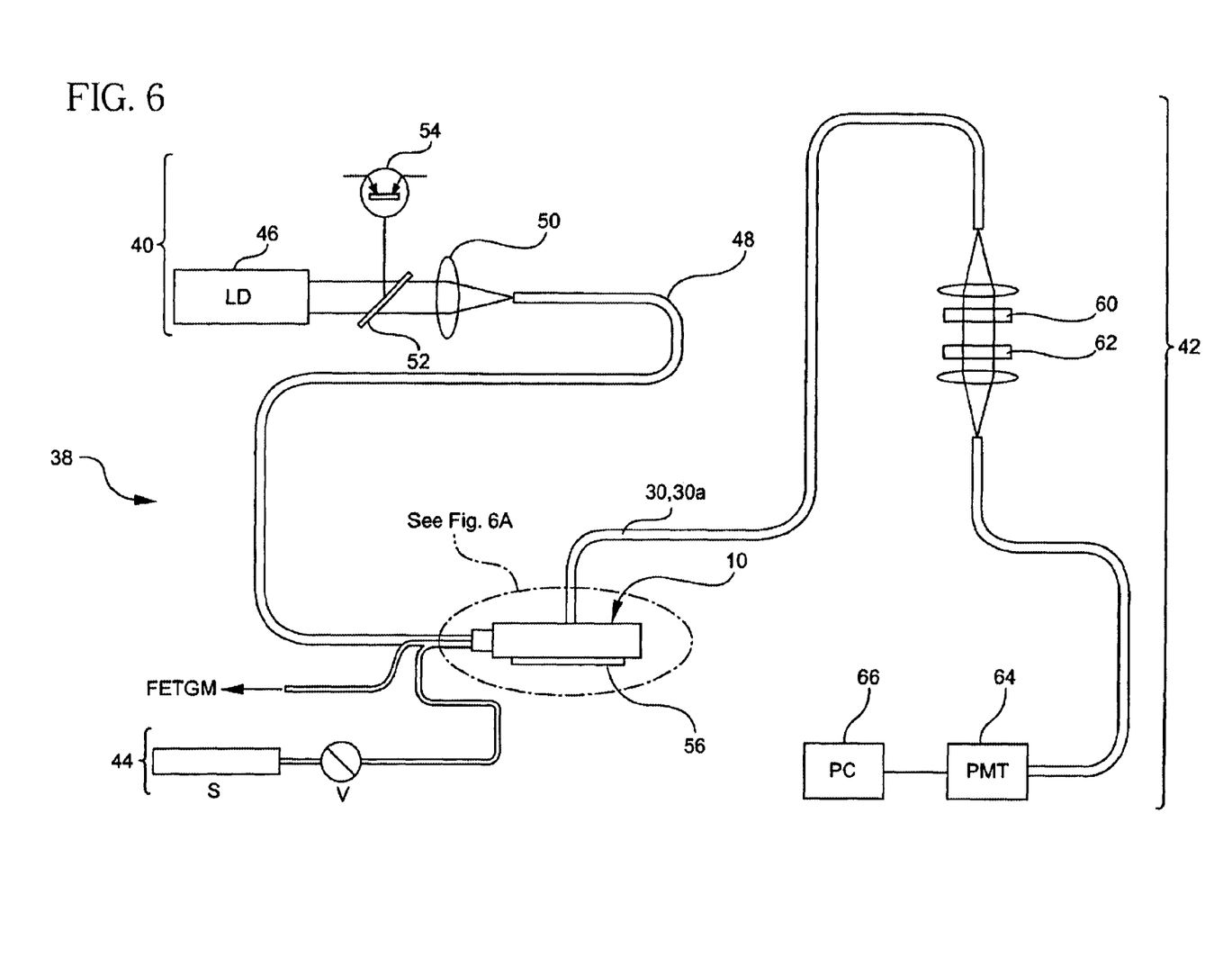
FIG. 6 is a schematic diagram of an exemplary fluorescence detection system utilizing the capillary waveguide fluorescence sensor of the present invention.
Figure 6A:
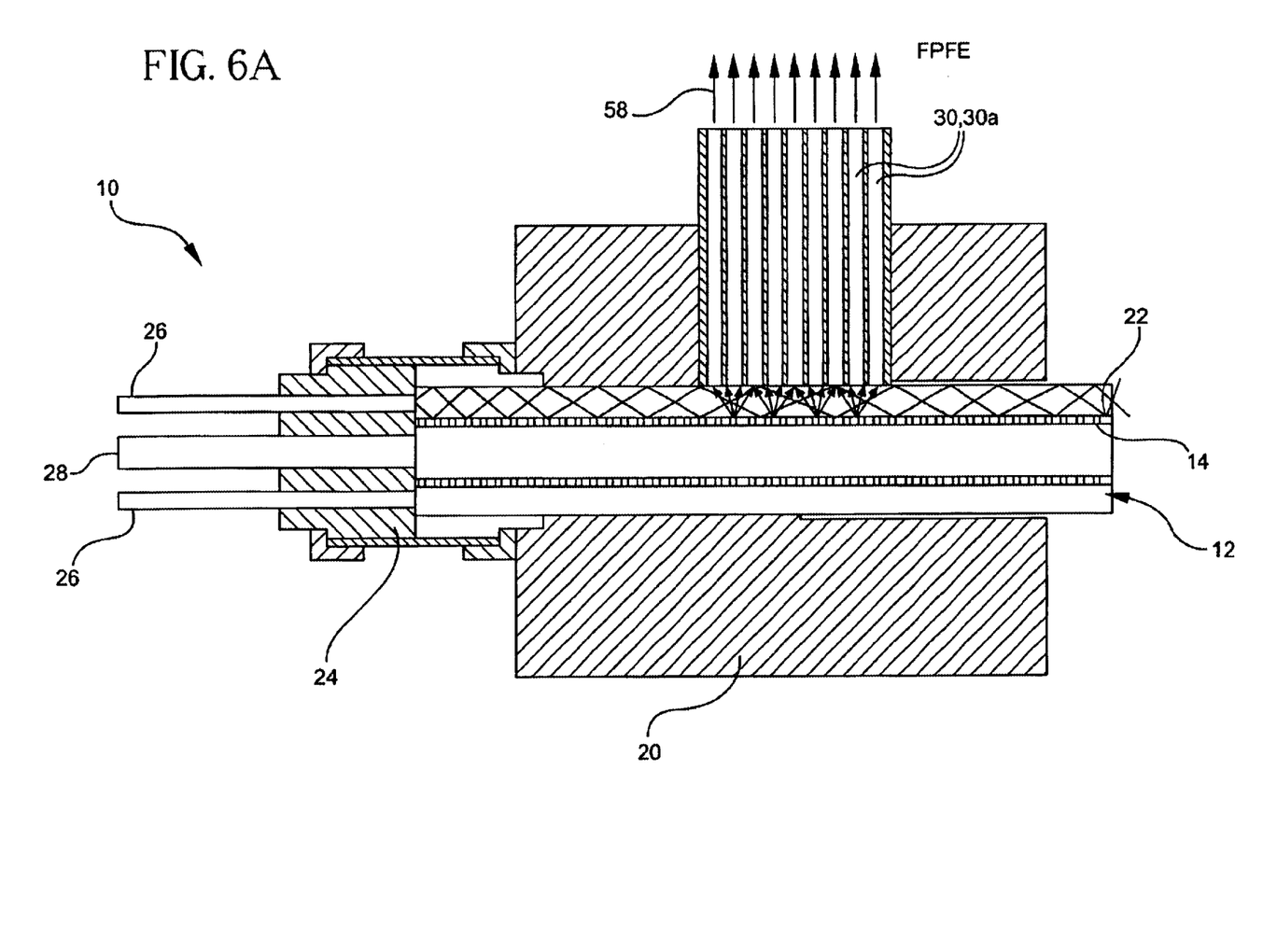
FIG. 6a is an enlarged view of the capillary waveguide fluorescence sensor shown in FIG. 6.

FIGS. 6 and 6a show an exemplary schematic of a fluorescence detection system 38 utilizing the capillary waveguide sensor 10 of the present invention. The system 38 further includes an optical system 40 for introducing the excitation light energy, an optical system 42 for capturing the fluorescence emission and a fluid control means 44 for controlling the flow of fluid containing the target sample through the capillary 12. An excitation light source 46 can be a DPSS laser (Midwest Laser Products model DPS10) operating at a wavelength of 532 nm with a maximum output optical power of 10 mW. Output of the laser is coupled into a 110 $\mu$m optical fiber 48 (Spectran Speciality Optics HCP110T) using a 20× microscope objective or a gradient index lens 50. Part of the incident excitation is reflected by a microscope slide 52 to a photodiode 54 for monitoring the stability of the laser output. The distal end of the optical fiber 48 forms a part of the optical/fluid connector 24 of the capillary waveguide sensor 10. The sensor 10 further includes a capillary 12 mounted into a polycarbonate cylindrical housing 20, which is heated using a strip heater 56.

Free propagating fluorescence 58 emanating from the surface of the capillary is collected by either a single one millimeter diameter optical fiber 30 with a NA=0.48 (Thorlabs URT1000) or a linear array 30a of preferably seventeen multimode fibers, each having a diameter of 300 microns and a NA=0.39(Spectran Speciality Optics HCP110T). Fluorescence emission is filtered using a combination of a holographic notch-plus filter 60 (Kaiser #HNPF) and a bandpass filter 62 (Omega Filters XF3074), providing over 50 dB rejection of the excitation energy. The optically filtered signal is detected by a photomultiplier 64 (Hamamatsu model HC120), which produces a stream of photoelectrons corresponding to the fluorescence intensity. A PC based real time counter 66 provides a count rate history of the fluorescence emission.

The detection system has a dark count of about 50 counts per second (cps) corresponding to an optical power of $2 \times 10^{-17}$ Watts. The system can operate up to a maximum count rate of $10^7$ cps giving a dynamic range of $10^6$. However, the upper limit can be easily increased through the use of scalers. In practice, the lower limit of detection is determined by the fluorescence background in the absence of the dye molecules. The signal is essentially obtained with a buffer solution, but in the presence of the excitation field. The background count rate can vary over a broad range, but is typically about 1000 cps.

In operation, the compact, portable and renewable fiber optic biosensor of the present invention can detect hybridization of nucleic acids on the interior surface of a microcapillary to quantitatively assay for the abundance and expression of specific genes in mixed microbial communities. Current prototypes use a micro-capillary flow cell to sense target molecules extracted from sampled bacterial cells. The flow cell permits exposure of a probe-coated surface to sample extracts, alternating with wash and regeneration solutions. However, the small size of the present invention is amenable to either temperature or chemical-composition control of hybridization stringency.

Hybridization can be detected by an array of collection fibers 30, coupled to a compact photomultiplier, as a fluorescence signal that preferentially emanates from the outer surface of the capillary. A competitive hybridization approach is used to measure the abundance of unlabelled sample rRNA or rDNA. It has been shown that the biosensor sensitivity is at least 30 pg/ml. It is anticipated that this sensitivity can be improved by more than an order of magnitude. Thus, the capillary waveguide fluorescence sensor of the present invention has sufficient sensitivity to detect: 1) specific bacteria (rRNA targeted); 2) a specific gene associated with a metabolic function (DNA targeted); or 3) the expression of a specific gene associated with a metabolic function (mRNA targeted) in small, easily processed samples, even when the genes are not particularly abundant.

As a result of the present invention, a compact fiber optic fluorescence sensor is provided for a multitude of applications, such as detection of microbial pathogens in air or liquids. The sensor can use a solid state laser as the excitation source and a single photon counting system to detect the weak fluorescent emission. The dynamic range is better than 50 dB. In one configuration the sensor allows for direct detection of the target species through fluorescence emission from a fluid, while another configuration uses hybridization of the target species to probes coated on the interior surface of the micro-capillary.

Although the illustrative embodiments of the present invention have been described herein with reference to the accompanying drawings, it is to be understood that the invention is not limited to those precise embodiments, and that various other changes and modifications may be effected therein by one skilled in the art without departing from the scope or spirit of the invention.

What is claimed is:

1. A fluorescence sensor comprising:
   a capillary having a capillary wall including an inner surface defining a capillary bore and an outer surface; and
   an optical/fluid connector connected to an end of said capillary, said optical/fluid connector including a fluid sample injection port for longitudinally injecting a fluid sample into said capillary bore and at least one light delivery optical fiber for longitudinally delivering light energy into said capillary.

2. A fluorescence sensor as defined in claim 1, further comprising at least one capillary outer surface collection optical fiber for collecting fluorescence emission from the fluid sample injected into said capillary bore, said at least one capillary outer surface collection optical fiber being positioned adjacent said outer surface of said capillary wall such that the central axis of said collection optical fiber is substantially perpendicular to the central axis of said capillary bore.

3. A fluorescence sensor as defined in claim 2, comprising a linear array of capillary outer surface collection optical fibers for collecting fluorescence emission from the fluid sample injected into said capillary bore, said linear array of capillary outer surface collection optical fibers including a plurality of aligned collection optical fibers positioned adjacent said outer surface of said capillary wall such that the central axes of said collection optical fibers are substantially perpendicular to the central axis of said capillary bore.

4. A fluorescence sensor as defined in claim 1, wherein said optical/fluid connector further includes a fluorescence collection optical fiber for longitudinally collecting fluorescence emission from the fluid sample injected into said capillary bore.

5. A fluorescence sensor as defined in claim 1, wherein said inner surface of said capillary wall is coated with a layer of probe molecules.

6. A fluorescence sensor as defined in claim 1, wherein said at least one light delivery optical fiber is positioned in said optical/fluid connector to longitudinally deliver the light energy into said capillary bore at said end of said capillary.

7. A fluorescence sensor as defined in claim 1, wherein said at least one light delivery optical fiber is positioned in said optical/fluid connector to longitudinally deliver the light energy into said capillary wall between said inner and outer surfaces at said end of said capillary.

8. A fluorescence sensor comprising:
   a capillary having a capillary wall including an inner surface defining a capillary bore and an outer surface; and
   an optical/fluid connector connected to an end of said capillary, said optical/fluid connector including a fluid sample injection port for longitudinally injecting a fluid sample into said capillary bore and at least one fluorescence collection optical fiber for longitudinally collecting fluorescence emission from the fluid sample injected into said capillary bore.

9. A fluorescence sensor as defined in claim 8, further comprising at least one capillary outer surface collection optical fiber for collecting fluorescence emission from the fluid sample injected into said capillary bore, said at least one capillary outer surface collection optical fiber being positioned adjacent said outer surface of said capillary wall such that the central axis of said collection optical fiber is substantially perpendicular to the central axis of said capillary bore.

10. A fluorescence sensor as defined in claim 9, comprising a linear array of capillary outer surface collection optical fibers for collecting fluorescence emission from the fluid sample injected into said capillary bore, said linear array of capillary outer surface collection optical fibers including a plurality of aligned collection optical fibers positioned adjacent said outer surface of said capillary wall such that the central axes of said collection optical fibers are substantially perpendicular to the central axis of said capillary bore.

11. A fluorescence sensor as defined in claim 8, wherein said optical/fluid connector further includes a delivery optical fiber for longitudinally delivering light energy into said capillary.

12. A fluorescence sensor as defined in claim 8, wherein said inner surface of said capillary wall is coated with a layer of probe molecules.

13. A fluorescence sensor as defined in claim 8, wherein said at least one fluorescence collection optical fiber is positioned in said optical/fluid connector to longitudinally collect the fluorescence emission from said capillary bore at said end of said capillary.

14. A fluorescence sensor as defined in claim 8, wherein said at least one fluorescence collection optical fiber is positioned in said optical/fluid connector to longitudinally collect the fluorescence emission from said capillary wall between said inner and outer surfaces at said end of said capillary.

15. A fluorescence sensor comprising:
    a capillary having a capillary wall including an inner surface defining a capillary bore and an outer surface;
    a fluid connector connected to an end of said capillary, said fluid connector including a fluid sample injection port for longitudinally injecting a fluid sample into said capillary bore; and
    at least one capillary outer surface collection optical fiber for collecting fluorescence emission from the fluid sample injected into said capillary bore, said at least one capillary outer surface collection optical fiber being positioned adjacent said outer surface of said capillary wall such that the central axis of said collection optical fiber is substantially perpendicular to the central axis of said capillary bore.

16. A fluorescence sensor as defined in claim 15, wherein said fluid connector further includes at least one optical fiber for longitudinally delivering light energy into said capillary or longitudinally collecting fluorescence emission from the fluid sample injected into said capillary bore.

17. A fluorescence sensor as defined in claim 16, wherein the fluid connector includes a delivery optical fiber for longitudinally delivering light energy into said capillary and a collection optical fiber for longitudinally collecting fluorescence emission from the fluid sample injected into said capillary bore.

18. A fluorescence sensor as defined in claim 16, wherein said at least one optical fiber is positioned in said fluid connector to longitudinally deliver the light energy into or longitudinally collect the fluorescence emission from said capillary bore at said end of said capillary.

19. A fluorescence sensor as defined in claim 16, wherein said at least one optical fiber is positioned in said fluid connector to longitudinally deliver the light energy into or longitudinally collect the fluorescence emission from said capillary wall between said inner and outer surfaces at said end of said capillary.

20. A fluorescence sensor as defined in claim 15, comprising a linear array of capillary outer surface collection optical fibers for collecting fluorescence emission from the fluid sample injected into said capillary bore, said linear array of capillary outer surface collection optical fibers including a plurality of aligned collection optical fibers positioned adjacent said outer surface of said capillary wall such that the central axes of said collection optical fibers are substantially perpendicular to the central axis of said capillary bore.

21. A fluorescence sensor as defined in claim 15, wherein said inner surface of said capillary wall is coated with a layer of probe molecules.

22. A method for sensing fluorescence emission from a fluid sample comprising the steps of:
    longitudinally injecting said fluid sample into a bore of a capillary having an inner surface and an outer surface;
    exciting said fluid sample by longitudinally delivering light energy into said capillary; and
    collecting fluorescence emission caused by said excitation from said fluid sample with at least one optical fiber positioned substantially perpendicularly to the central axis of said capillary bore.

23. A method as defined in claim 22, further comprising the step of coating said inner surface of said capillary with a layer of probe molecules, said inner surface of said capillary defining said capillary bore.

24. A method as defined in claim 22, wherein the light energy is longitudinally delivered into said capillary bore at an end of said capillary.

25. A method as defined in claim 22, wherein the light energy is longitudinally delivered into a wall of said capillary between said inner and outer surfaces of said capillary, said inner surface of said capillary defining said capillary bore.

26. A method as defined in claim 22, further comprising the step of collecting fluorescence emission caused by said excitation from said fluid sample with at least one optical fiber positioned substantially parallel to the central axis of said capillary bore.

27. A method as defined in claim 22, wherein said step of collecting fluorescence emission caused by said excitation from said fluid sample is accomplished with a linear array of collection optical fibers, said linear array of collection optical fibers including a plurality of aligned collection optical fibers positioned adjacent said outer surface of said capillary such that the central axes of said collection optical fibers are substantially perpendicular to the central axis of said capillary bore.

28. A method for sensing fluorescence emission from a fluid sample comprising the steps of:
    longitudinally injecting said fluid sample into a bore of a capillary having an inner surface and an outer surface;
    exciting said fluid sample by longitudinally delivering light energy into said capillary; and
    longitudinally collecting fluorescence emission caused by said excitation from said fluid sample with at least one optical fiber positioned substantially parallel with the central axis of said capillary bore.

29. A method as defined in claim 28, further comprising the step of perpendicularly collecting fluorescence emission caused by said excitation from said fluid sample with at least one optical fiber positioned substantially perpendicularly to the central axis of said capillary bore.

30. A method as defined in claim 29, wherein said step of perpendicularly collecting fluorescence emission caused by said excitation from said fluid sample is accomplished with a linear array of collection optical fibers, said linear array of collection optical fibers including a plurality of aligned collection optical fibers positioned adjacent said outer surface of said capillary such that the central axes of said collection optical fibers are substantially perpendicular to the central axis of said capillary bore.

31. A method as defined in claim 28, wherein the light energy is longitudinally delivered into a wall of said capillary between said inner and outer surfaces of said capillary, said inner surface of said capillary defining said capillary bore.

32. A method as defined in claim 28, further comprising the step of coating said inner surface of said capillary with a layer of probe molecules, said inner surface of said capillary defining said capillary bore.

33. A method as defined in claim 28, wherein the light energy is longitudinally delivered into said capillary bore at an end of said capillary.

* * * * *